United States Patent
Carlson, III

(10) Patent No.: US 6,966,818 B1
(45) Date of Patent: Nov. 22, 2005

(54) DIRECT CLAMP TOOLING FOR ROBOTIC APPLICATIONS

(75) Inventor: Glenn A. Carlson, III, Auburn Hills, MI (US)

(73) Assignee: Acme Manufacturing Company, Auburn Hills, MI (US)

( * ) Notice: Subject to any disclaimer, the term of this patent is extended or adjusted under 35 U.S.C. 154(b) by 0 days.

(21) Appl. No.: 10/967,914

(22) Filed: Oct. 18, 2004

(51) Int. Cl.[7] .............................................. B24B 51/00
(52) U.S. Cl. .......................... 451/5; 451/365; 451/460
(58) Field of Search .......................... 451/5, 11, 12, 24, 451/67, 365, 460, 914; 29/558, 559, 527.6

(56) References Cited

U.S. PATENT DOCUMENTS

| | | | | |
|---|---|---|---|---|
| 4,827,674 A | * | 5/1989 | Vanderwal et al. | ......... 451/365 |
| 4,982,939 A | * | 1/1991 | Yoshikawa et al. | ........... 269/32 |
| 6,170,895 B1 | * | 1/2001 | Schopp et al. | ................. 294/88 |
| 6,394,880 B1 | * | 5/2002 | Basler et al. | .................. 451/28 |
| 2002/0159868 A1 | * | 10/2002 | Nadicksbernd | ............. 414/292 |

* cited by examiner

*Primary Examiner*—Jacob K. Ackun, Jr.
(74) *Attorney, Agent, or Firm*—Harness, Dickey & Pierce, P.L.C.

(57) ABSTRACT

A direct clamp robotic finishing system is provided including a robot, a gripper secured to the robot, and a pair of fingers secured to the gripper. A tray assembly is also provided for supporting a plurality of implants for picking up by the fingers. An implant reorientation station is provided for supporting the implant being maneuvered by the robot as the robot re-grips the implant from a new direction. The fingers directly clamp the implant thereby eliminating the need for dedicated implant support bars.

1 Claim, 11 Drawing Sheets

DIRECT CLAMP TOOLING FOR ROBOTIC APPLICATIONS

FIELD OF THE INVENTION

The present invention relates to robotic finishing systems and, more particularly, to direct clamp tooling for robotic prosthetic knee finishing systems.

BACKGROUND OF THE INVENTION

Metalworking of cast metal articles such as prosthetic knee implants typically requires surface finishing such as buffing, polishing, deburring, grinding and satin finishing. Traditionally, these finishing steps were performed by hand. More recently, however, automated processing replaced most manual operations. As compared to manual finishing, automated finishing provides greater efficiency, precision, and safety.

An important aspect of robotic finishing knee implants is the need to manipulate the implant to expose all surfaces to a finishing device such as a wheel or belt. To accomplish this, the implant must be held by the robot and maneuvered to various orientations relative to the finishing device. Importantly, the robot must hold the implant against the finishing device with pressure yet not mar the surface of the implant when picking it up or putting it down.

One technique for enabling a knee implant to be picked up and manipulated by a robot in a finishing operation is to mount the knee implant to a metal support bar. In this technique, the knee implant is fixed to a central region of a metal bar through the use of fasteners such as screws. The bar laterally extends beyond the both outboard edges of the knee implant to provide two graspable handles for the robot. The robot may then use jaws to clamp onto one handle of the bar and manipulate the knee implant relative to the finishing device. The knee implant and bar assembly may then be set down while the robot repositions its jaws to the other graspable handle of the bar. The knee implant may then be further manipulated relative to the finishing device.

While the use of support bars for finishing knee implants has been widely accepted, there is room for improvement in the art. For example, each knee implant must be fixed to a dedicated support bar by way of fasteners such as screws. This is a labor intensive process. Also, one support bar must be provided for every knee implant in a particular batch to be finished. Assuming that twelve knee implants are provided in each batch and finishing operations continue throughout the various working shifts, a large number of bars must be kept in stock. Also, since the finishing process wears the support bars, each support bar must be periodically replaced. Given the large number of bars in a typical inventory, this can be expensive.

In view of the forgoing, it would be desirable to provide a tooling system for enabling the direct clamping of knee implants to thereby eliminate the need for support bars.

SUMMARY OF THE INVENTION

The above and other objects are provided by a direct clamp robotic finishing system comprising a robot, a gripper secured to the robot, and fingers secured to gripper. The gripper and fingers are operable in an open mode and a closed mode for gripping an implant. A tray assembly is also provided for supporting a plurality of implants for picking up by the fingers. An implant reorientation station supports the implant being maneuvered by the robot as the robot re-grips the implant from a new direction.

In accordance with the teachings of the present invention, at least one implant is moved from a loading area to the interior of a robotic cell by way of the tray assembly. The tray assembly is configured to support the knee implants in a pre-selected orientation and with minimum contact so as not to mar the surface of any pre-finished surfaces. The robot moves the fingers to the implant in an open mode and when properly oriented relative to the implant, switches the fingers to a closed mode so that the fingers abutingly engage clampable surfaces of the implant. The robot may then lift and manipulate the implant relative to a finishing device. Upon completion of a first finishing process, the robot places the implant on the implant reorientation station and moves the fingers to an open mode. The implant reorientation station minimally contacts the implant so not to mar any pre-finished surfaces. The robot then re-orients the fingers and re-grips the implant from a direction 180 degrees relative to the initial gripping direction. A subsequent finishing process may then be performed. Advantageously, no implant support bar need be secured to the implant for the finishing process. Further, improved trays and implant reorientation stations are employed since an implant support bar no longer needs to be accommodated.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
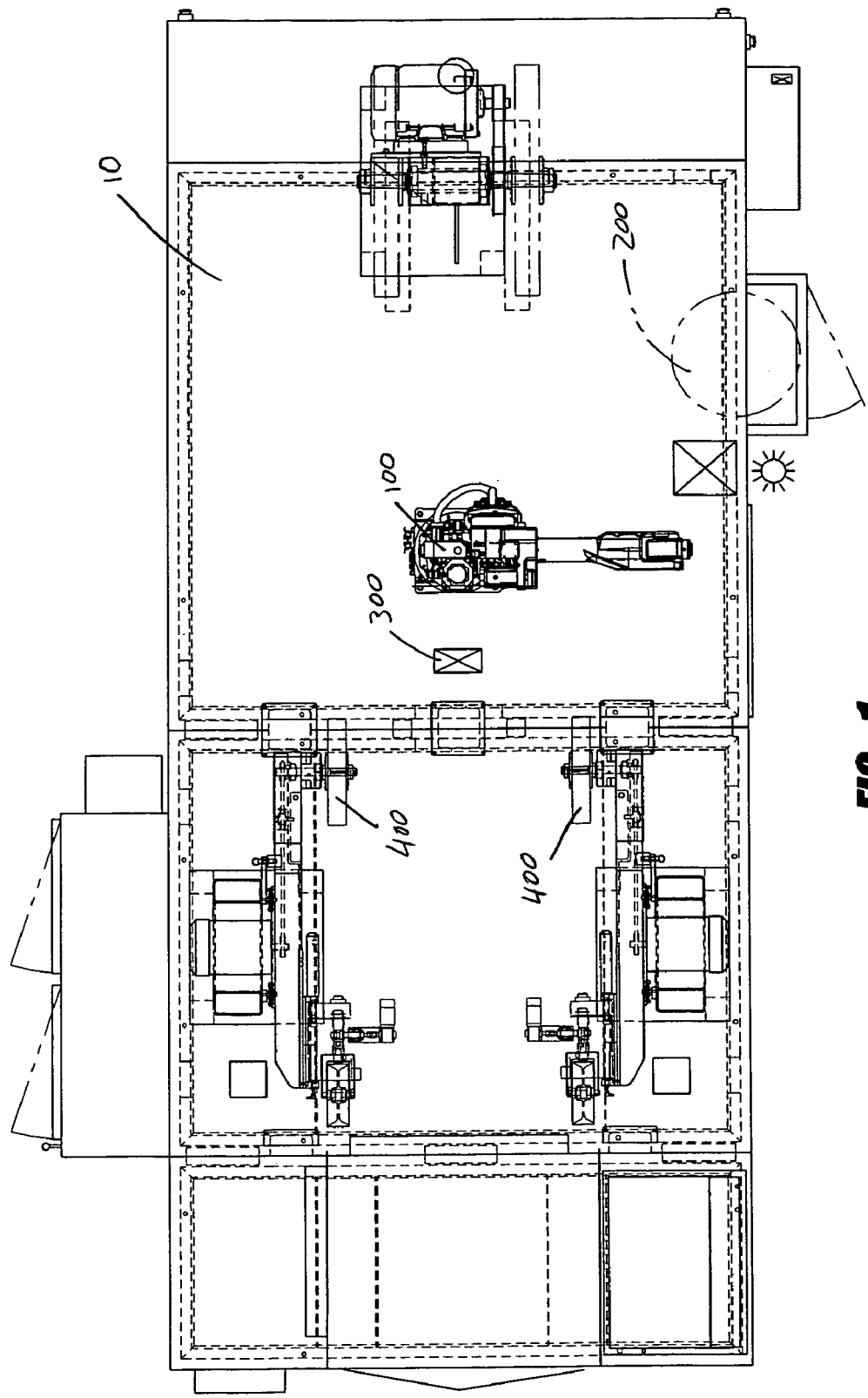
FIG. 1 is an illustration of a robotic cell including the tooling of the present invention.

Referring to the drawings, FIG. 1 illustrates a robotic cell 10 used for robotically finishing metal articles such as knee implants. The cell 10 includes a robot 100, a revolving implant supply device 200, an implant reorientation station 300, and two finishing devices 400 in the form of stacked wheel heads. In operation, the robot 100 picks up a knee implant from the revolving part supply device 200 and manipulates the implant relative to the finishing devices 400 to perform buffing, polishing, and the like. To expose all surfaces of the implant to the finishing devices 400, the robot 100 sets the implant down on the implant reorientation station 300 and picks it back up from an opposite side. Finishing operations are thereafter continued.

Although other robots may be employed, it is presently preferred to employ a Fanuc M16iB Robot with a 20 kg payload. Further, although stacked wheel heads are described above as the finishing devices 400, other finishing apparatuses may substitute therefore. Finally, although a knee implant is used throughout this description as an example of the part to be finished, the present invention is not limited to tooling for finishing knee implants.

Figure 2:
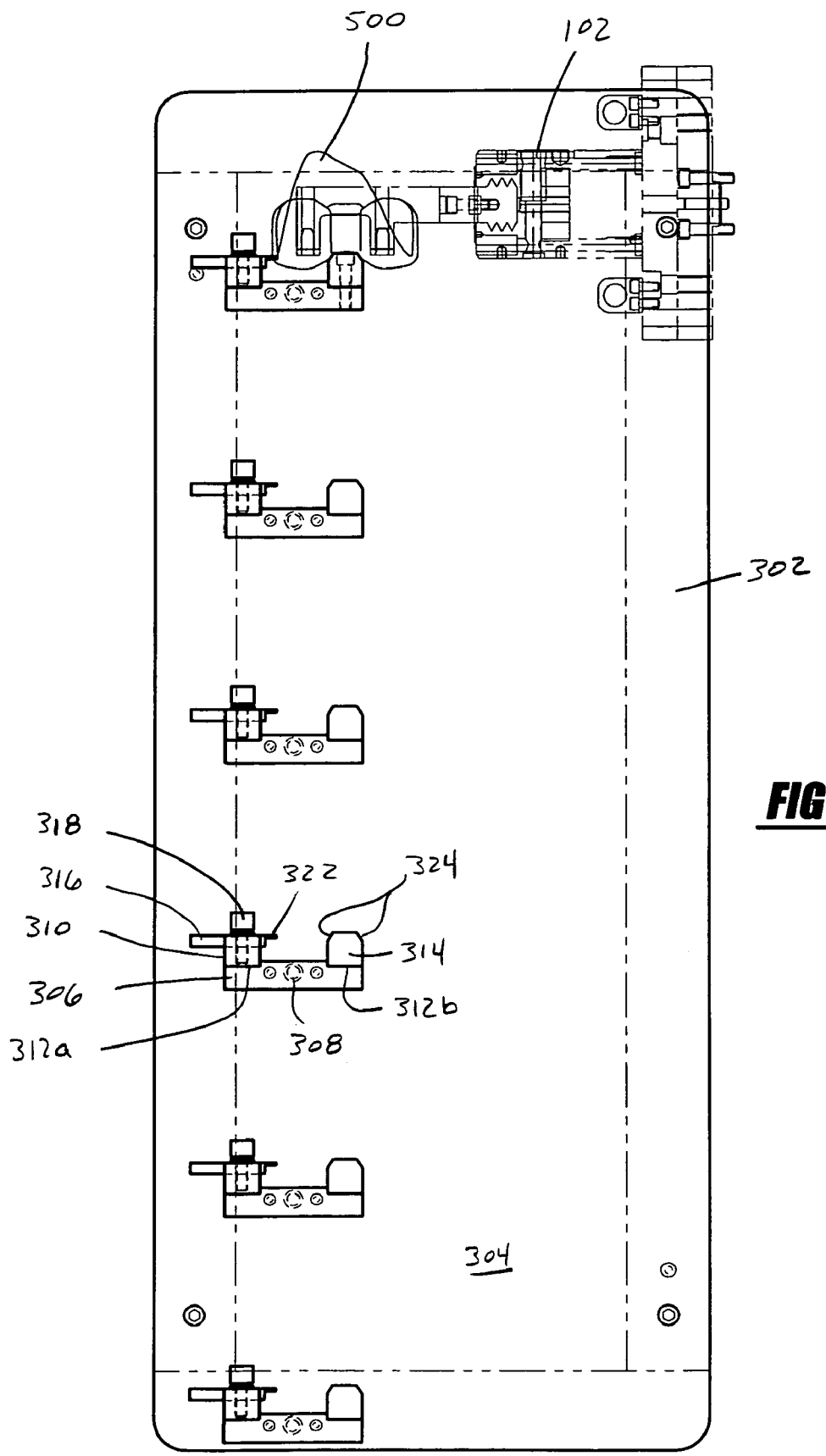
FIG. 2 is a front view of a tray assembly of the present invention.
Figure 3:
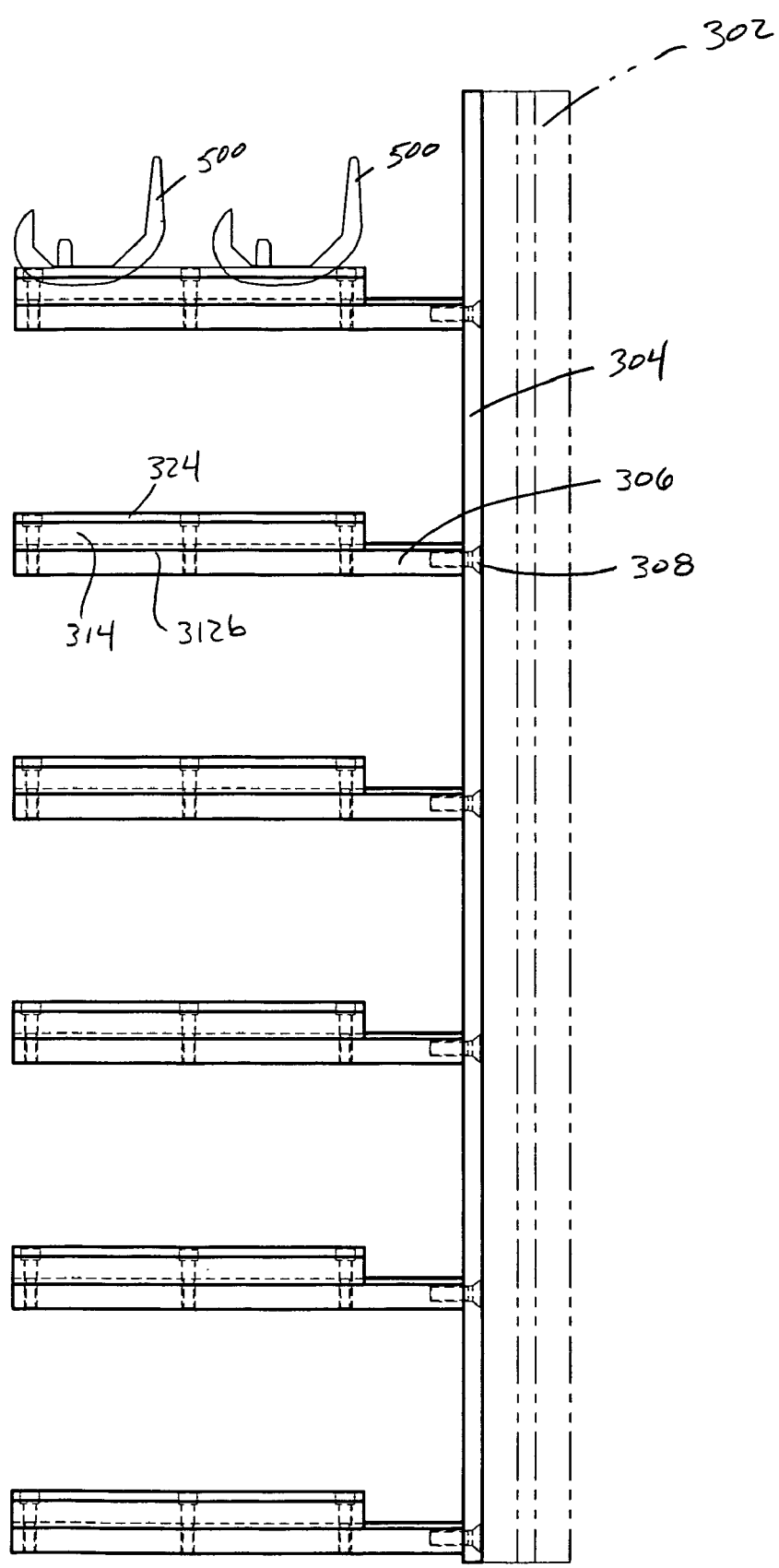
FIG. 3 is a side view of the tray assembly of the present invention.
Figure 4:
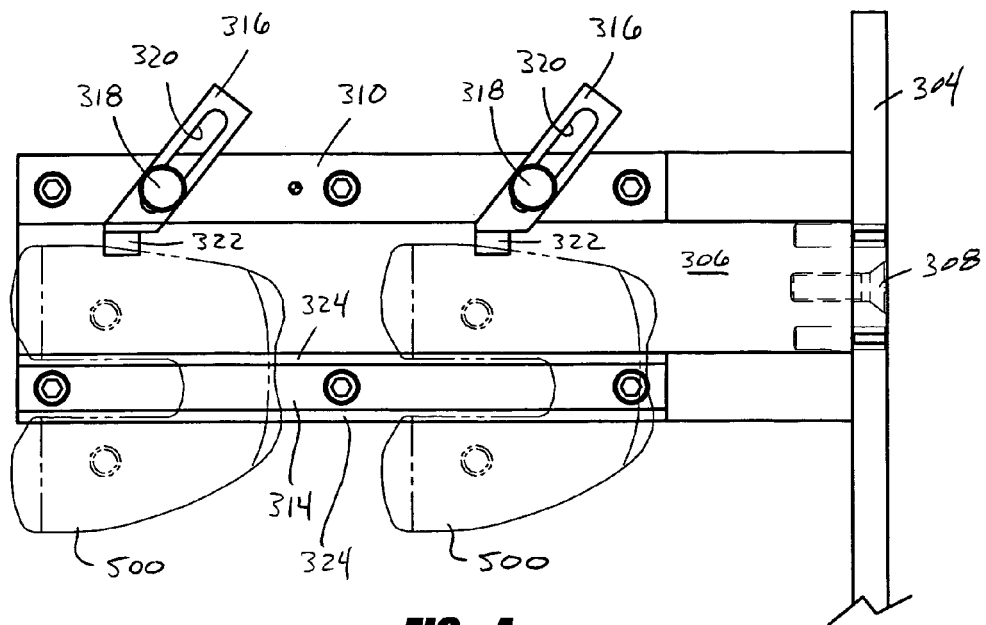
FIG. 4 is a plan view of part of the tray assembly of the present invention.

Turning now to FIGS. 2–4, a tray assembly 302 of the revolving implant supply device 300 is illustrated. The tray assembly 302 includes a vertically oriented base plate 304 formed of, for example, aluminum. A plurality of vertically spaced apart mounting plates 306 are independently fixed to the base plate 304 by fasteners 308 such as screws. In the illustrated example, six base plates 304 are cantilevered to the base plate 304.

Each mounting plate 306 includes a slide block 310 mounted to a first channel 312a formed along a first outboard edge of the top surface of the mounting plate 306 by fasteners such as recessed screws. The slide block 310 may be formed of, for example, hot rolled steel. Each mounting plate 306 also includes a part support 314 mounted to a second channel 312b formed along a second outboard edge of the top surface of the mounting plate 306 by fasteners such as recessed screws. The part support 314 may be formed of, for example, Teflon (Registered Trademark) and is preferably disposed parallel to and laterally spaced apart from the slide block 310.

A pair of adjustable part locators 316 are mounted to each slide block 310 by way of fasteners 318 in the form of, for example, knurled head screws. Each part locator 316 includes a slot 320 to accommodate the associated fastener 318 and enabling fore and aft movement relative to the slide block 310. Each part locator 316 also includes a tang 322 projecting therefrom and adapted to abuttingly engage a relieved surface of the implant 500. The tang 322 preferably projects orthogonally relative to the slide block 310 to position the implant 500 in a pre-selected location and orientation on the part support 314 for consistent gripping by the gripper 102. The tang 322 also prevents the implant 500 from tilting in one direction when rotating with the base plate 304 or when grabbing by the gripper 102. The tang 322 provides a stop that can be exploited when applying pressure to the implant 500 during the grabbing sequence.

The part support 314 includes a pair of chamfered edges 324 for abuttingly engaging the implant 500 along pre-selected areas which will later be subject to polishing. This ensures that the part support 314 does not mar the surface of the implant 500 which could require further processing. The width of the part support 314 and, in particular, the pair of chamfered edges 324 is carefully selected relative to the patella groove of the implant 500. In particular, the chamfered edges 324 support the implant 500 without contacting the inboard flat surfaces along the patella groove which are typically pre-finished.

The height of the part support 314 is also carefully selected to provide sufficient clearance between the implant 500 and the mounting plate 306 to allow the implant 500 o be tipped toward the mounting plate 306 during the grabbing sequence. This enables the implant 500 to clear the tang 322 and be removed from the support part 314. This clearance is also carefully selected to limit the maximum tipping of the implant 500 toward the mounting plate 306 within a given tolerance. The tolerance is controlled so that the implant 500 tends to return to horizontal during the grabbing sequence. In this event, the tang 322 acts as a stop.

The part support 314 is laterally spaced apart from the slide block 310 by a distance more than adequate to support the widest implant 500 expected to be finished. More narrow implants 500 can be supported equally as well by adjusting the position of the part locators 316. Advantageously, implants 500 of all widths are supported along a common center line by the part support 314.

Figure 5:
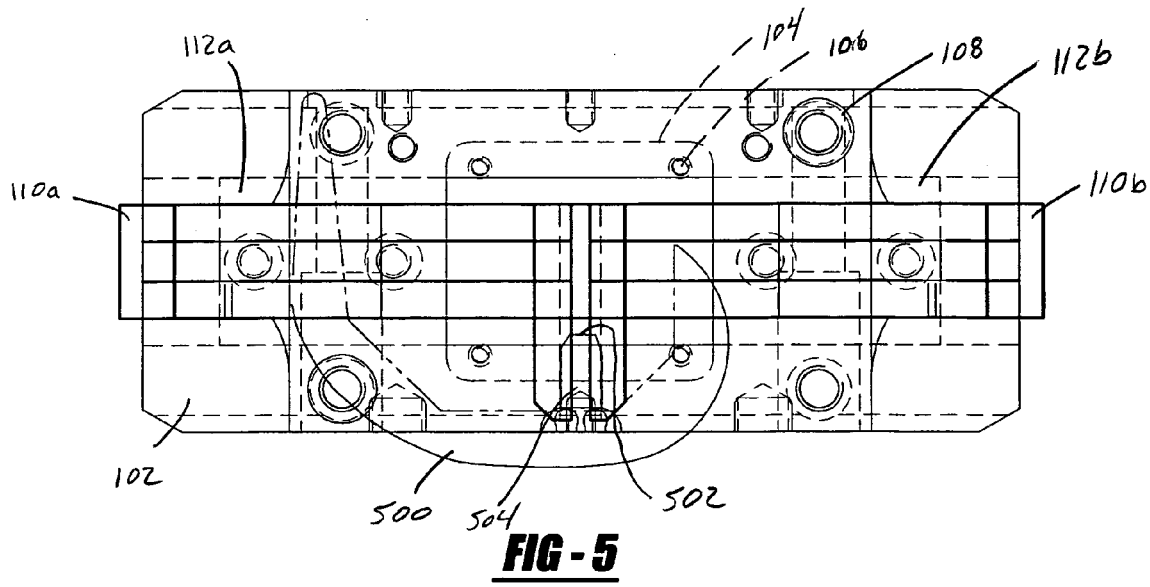
FIG. 5 is a front view of a gripper and finger assembly of the present invention.
Figure 6:
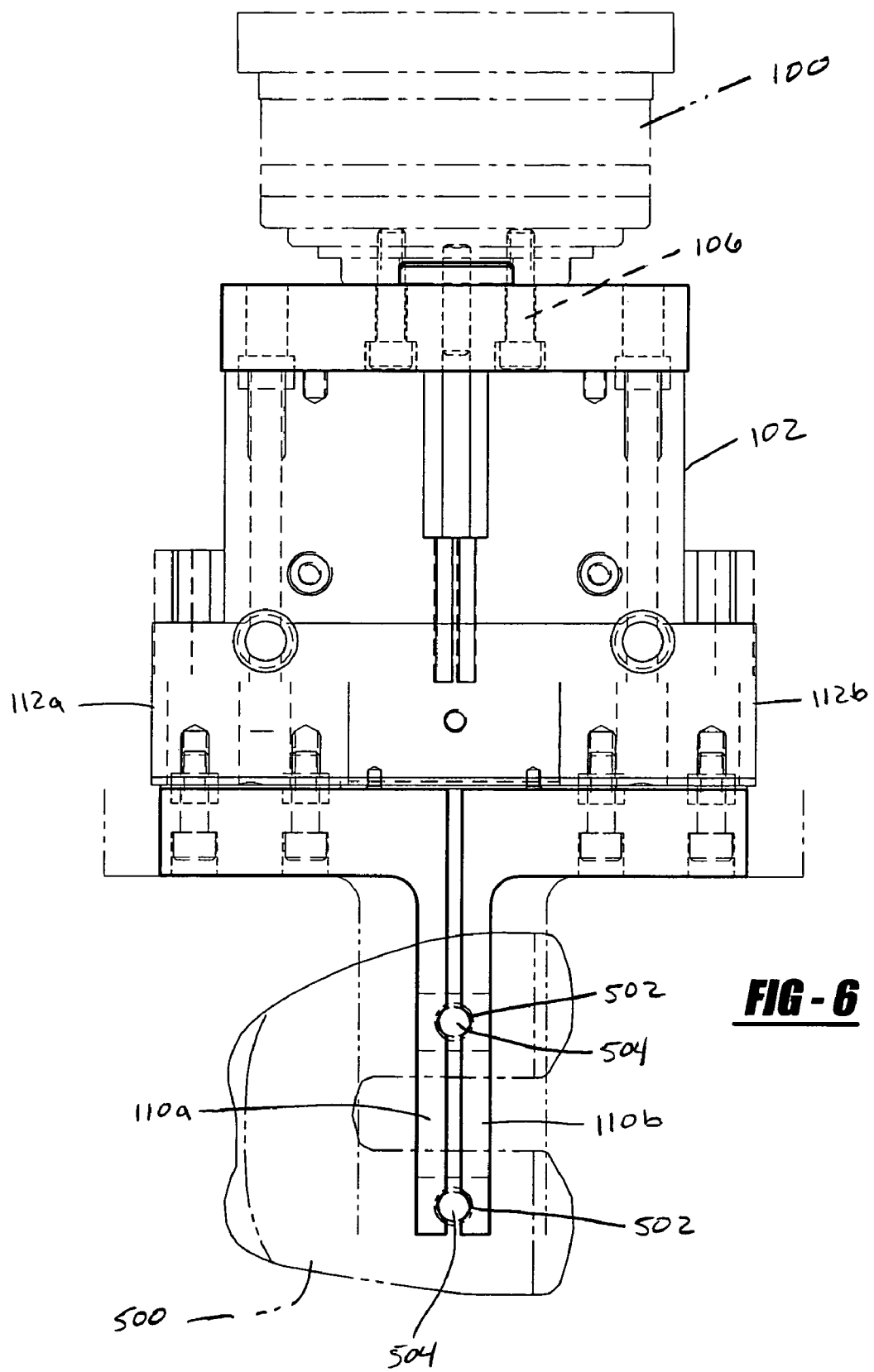
FIG. 6 is a plan view of the gripper and finger assembly of the present invention.

Turning now to FIGS. 5 and 6, a detailed view of the gripper 102 of the robot 100 is illustrated. The gripper 102 is preferably a Schunk Parallel Gripper, PGN series, stroke 1, with a spring to close (#PGN Plus 125 1/AS #371-403). The gripper 102 is fixed to the end of the robot 100 by an adapter plate 104. Preferably, screws 106 pass through the adapter plate 104 and into the robot 100 while screws 108 pass through the adapter plate 104 and into a first end of the gripper 102.

A pair of L-shaped fingers 110 is fixed to a second end of the gripper 102 opposite the robot 100. The first finger 110a is fixed to one outboard end 112a of the gripper 102 while the second finger 110b is fixed to a second outboard end 112b of the gripper 102. The gripper 102 is pneumatically operated to move the fingers 110 between an open mode (shown in phantom in FIG. 6) and a closed mode (shown in solid in FIG. 6). In an open mode, the fingers 110 are pneumatically biased outwardly to allow the fingers 110 to fit on opposite sides of a clampable surface 502 of the implant 500. In a closed mode, the fingers 110 are pneumatically biased inwardly to allow the fingers 110 to abuttingly engage the clampable surface 502 of the implant 500.

The clampable surface 502 is not particularly limited to any specific configuration and most projections will suffice. In some versions, the implant 500 is provided with posts 504 used during an operation to secure the implant 500 to a patient. Posts 504 provide an ideal clampable surface 502. In other versions, threaded openings are provided within the implant 500. These threaded openings can be fit with threaded members (see FIG. 14) to provide the clampable surface 502. In yet another version, a box-shaped projection may be present within the implant 500. This box may also serve as the clampable surface 502.

The gripper 102 preferably includes a spring (not shown) biasing the fingers 110 toward one another. In the unlikely event pneumatic force is lost, the spring urges and/or maintains the fingers 110 in the closed mode. This prevents the implant 500 from being dropped and potentially damaged. The gripper 102 also preferably includes a proximity switch (not shown) that senses the relative position or state of the fingers 110. In this way, the proximity switch can be used to determine whether or not the implant 500 is being clamped by the fingers 110.

It should be noted that the gripper 102 has a fully open position, a fully closed position, and a working position between the fully open and fully closed positions. In the working position, the gripper 102 is in a state suitable for clamping the clamping surface of the implant 500 but still has a distance to go to reach the fully closed position. The fingers 110 do not abut one another in the working position. Advantageously, this "gapped" working position prevents the fingers 110 from wearing on one another to increase their usable working life.

Turning now to FIGS. 7–10, an exemplary embodiment of the fingers 110 is illustrated. Although other materials are available, it is presently preferred that the fingers 110 be made of a pre-hardened alloy steel. Each of the fingers 110 is generally L-shaped and includes a mounting leg 114 extending essentially orthogonally relative to a clamping leg 116. The inboard transition between the mounting leg 114 and the clamping leg 116 is preferably radiused to increase strength and wearability.

Figure 9:
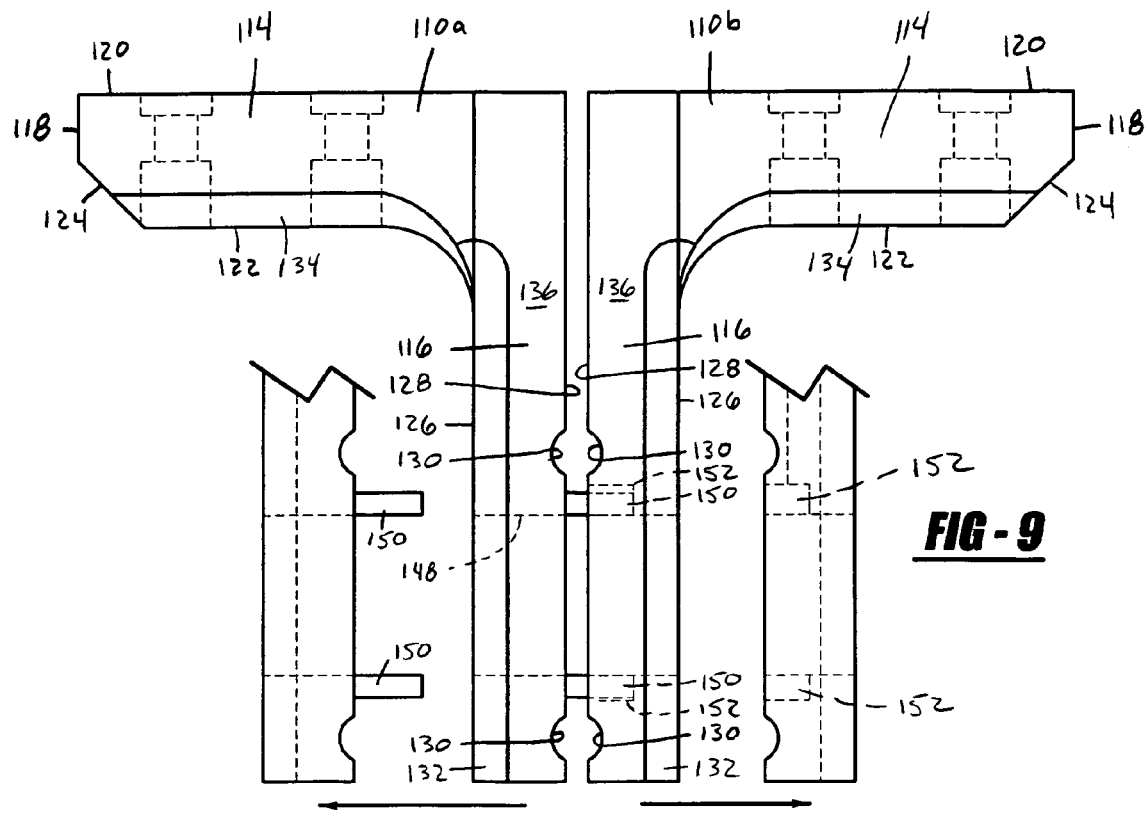
FIG. 9 is a top view of the finger assembly of the present invention with the fingers shown in an open and closed mode.

As best viewed in FIG. 9, the outboard edge 118 of each mounting leg 114 extends substantially perpendicular to a mounting surface 120. The front face 122 of each mounting leg 114 extends substantially perpendicular to the outboard edge 118 and parallel to the mounting surface 120. The transition between the outboard edge 118 and the front face 122 is chamfered to form a corner surface 124. Preferably, the corner surface 124 angles at about 45 degrees relative to the outboard edge 118 and the front face 122.

An outboard face 126 of each clamping leg 116 extends substantially perpendicular to the mounting surface 120. A working surface 128 of each clamping leg 116 extends substantially parallel to the outboard face 126. Each working surface 128 includes a pair of spaced apart clamping channels 130. The channels 130 compliment one another to form a clam shell gripping surface when the fingers 110 are brought close together. Although the channels 130 are illustrated with a constant depth relative to the working surface 128, the channels 130 may be tapered to provide a tapered clam shell gripping surface. The channels 130 preferably compliment the shape of the clampable surface of the implant as much as possible.

Figure 7:
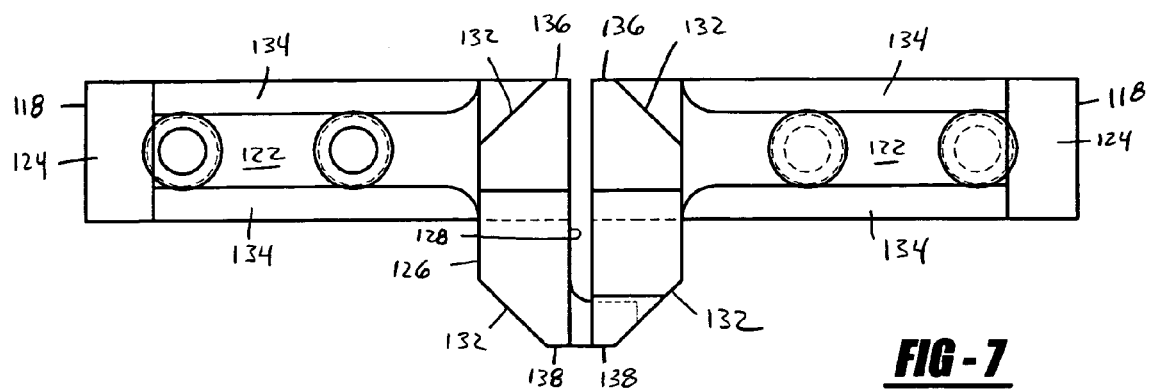
FIG. 7 is a front view of a finger assembly of the present invention.

As best seen in FIG. 7, chamfered sidewalls 132 extend at an angle between the working surface 128 and the outboard face 126. Similarly, chamfered sidewalls 134 extend at an angle between the front face 122 and the mounting surface 120. This yields a substantially trapezoidal cross section to the mounting leg 114 and clamping leg 116. Of course, a relatively small top surface 136 and a relatively small bottom surface 138 are provided between the sidewalls 132 and the working surface 128. Similarly, a top surface 140 and a bottom surface 142 are provided between the sidewalls 134 and the mounting surface 120.

Figure 8:
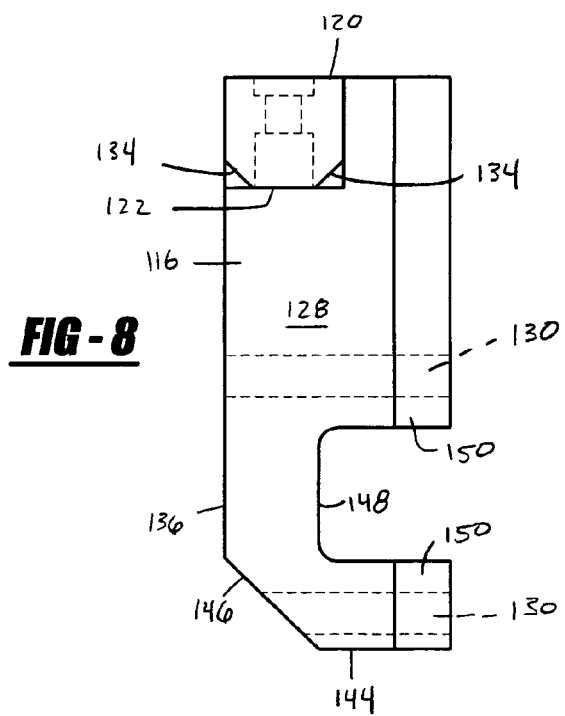
FIG. 8 is a side view of one finger of the finger assembly of the present invention.
Figure 10:
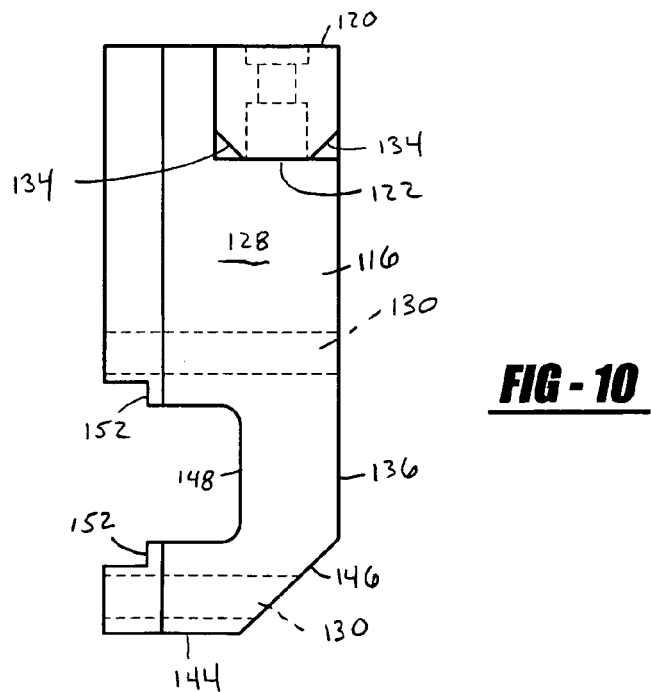
FIG. 10 is a side view of the other finger of the finger assembly of the present invention.

As best seen in FIGS. 8 and 10, each clamping leg 116 includes a front end face 144 extending substantially perpendicular to the working surface 128 and parallel to the mounting surface 120. An angled surface 146 extends between the front end face 144 and the top surface 136. A substantially square shaped opening 148 is formed within each clamping leg 116 from the working surface 128. The opening 148 accommodates a box that is often provided within knee implants (between the clampable surfaces) so that the box and the fingers 110 do not interfere.

A pair of pins 150 extends from the clamping leg 116 orthogonal to the working surface 120 of the first finger 110a. Complimentary slots 152 are provided in the second finger 110b for receiving the pins 150 (both modes are illustrated in FIG. 9). The pins 150 provide a greater contact surface area compared to the bottom surfaces 138 of the fingers 110 which are separated by a gap. As such, a line contact can be established with the implant just prior to clamping.

The many chamfered surfaces of the fingers 110 increase the clearance between the fingers 110 and the finishing devices used to finish the implant gripped by the fingers 110. Maximum attention is paid to robustness and wearability juxtaposed with interference concerns.

Figure 11:
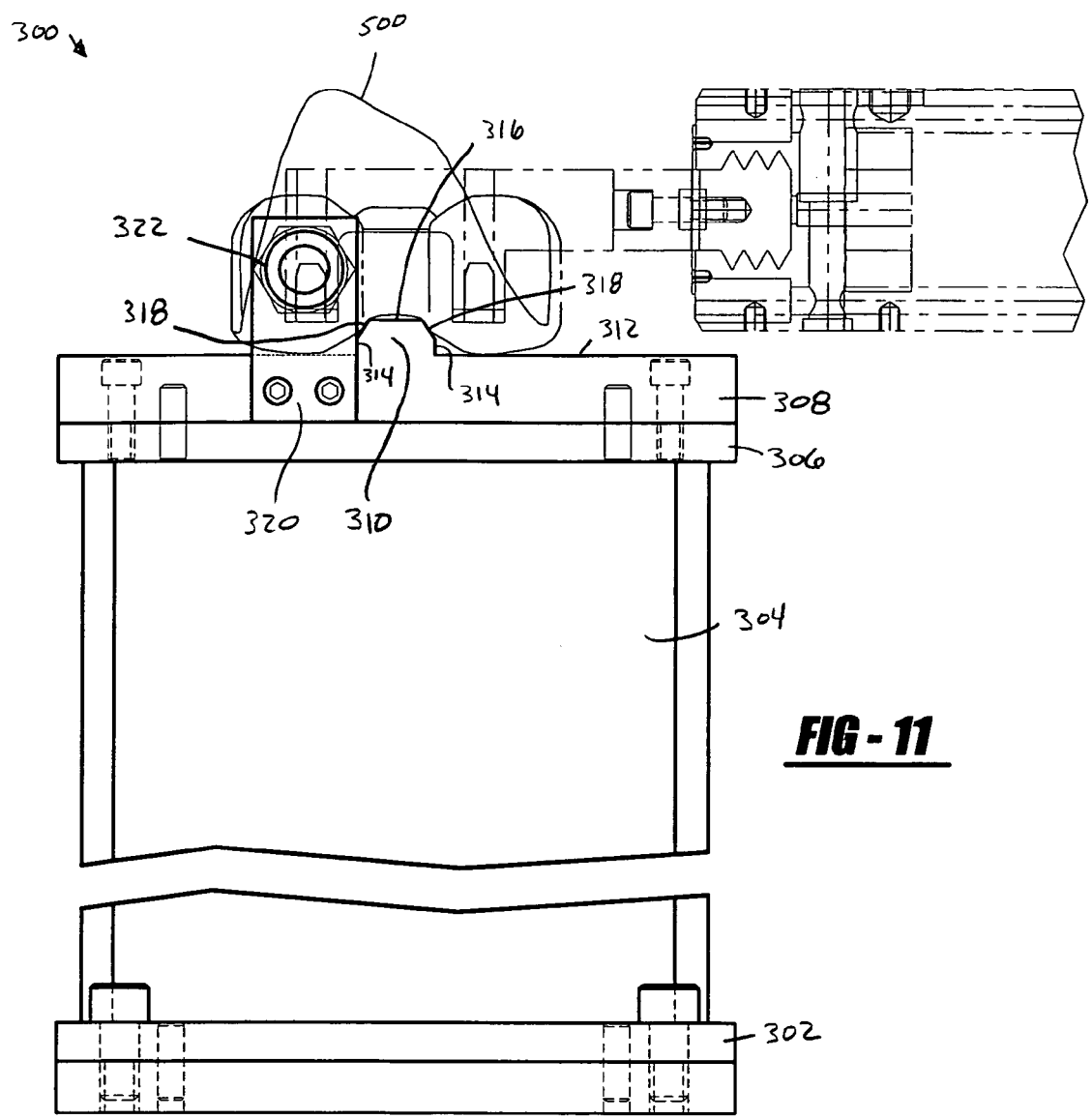
FIG. 11 is a front view of an implant reorientation station of the present invention.
Figure 12:
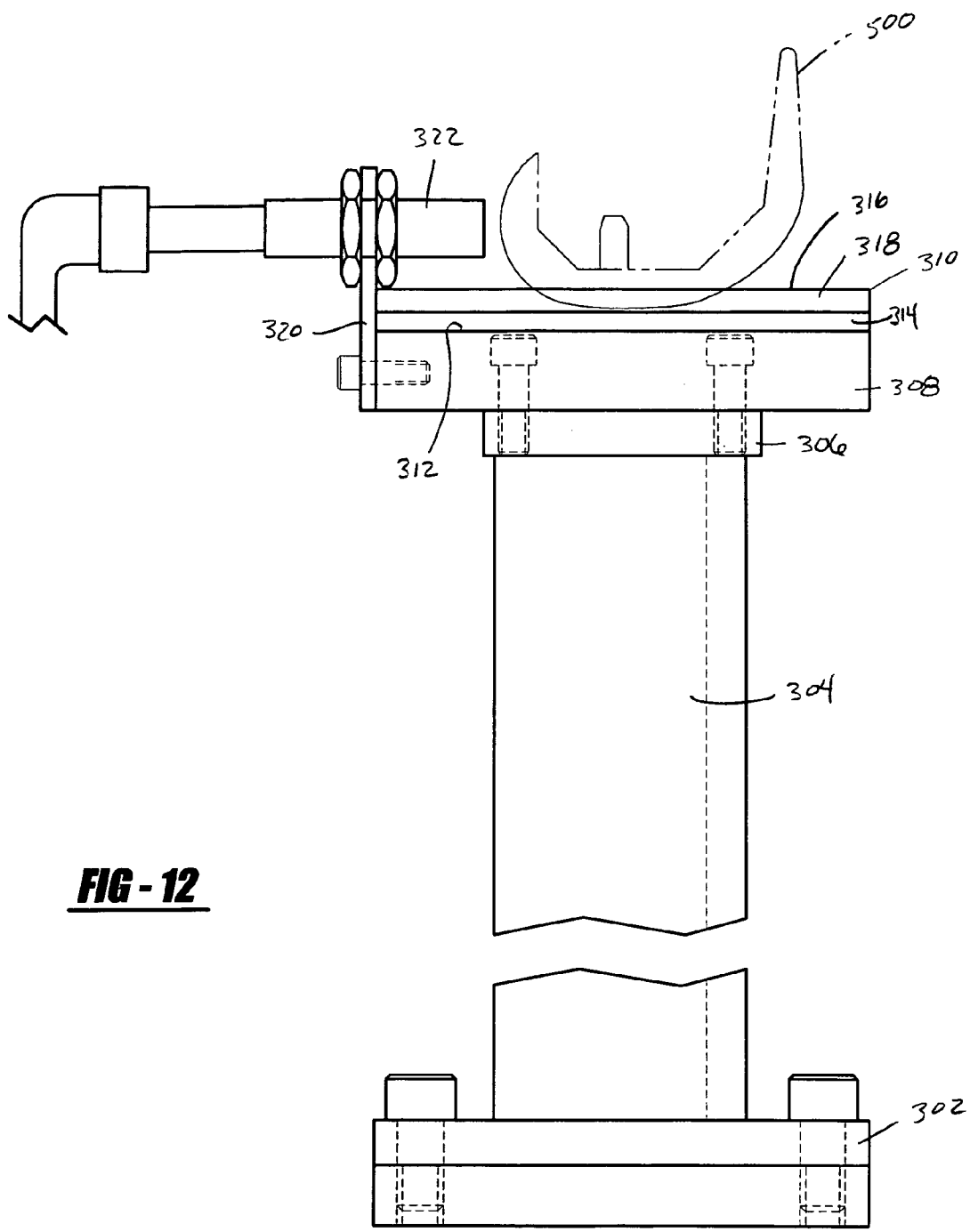
FIG. 12 is a side view of the implant reorientation station of the present invention.
Figure 13:
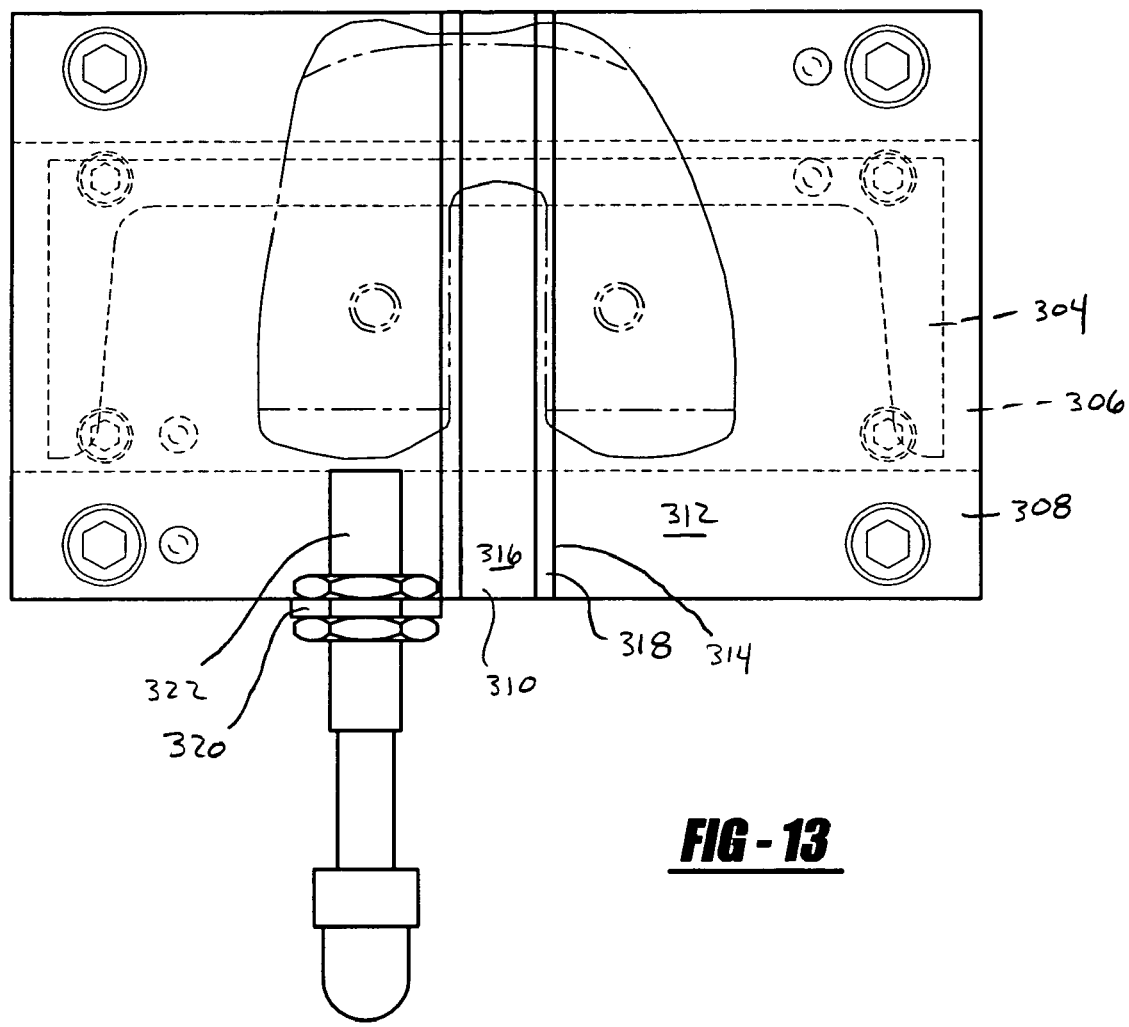
FIG. 13 is a plan view of the implant reorientation station of the present invention.

Turning now to FIGS. 11–13, the implant reorientation station 300 is shown in greater detail. The station 300 includes a base 302 securable to a floor and a generally U-shaped riser 304 extending substantially vertically from the base 302. A top plate 306 is secured to the riser 304 opposite and substantially parallel to the base 302.

A turnaround support 308 is fixed to the top plate 306 by fasteners such as screws. The turnaround support 308 includes a, e.g., Teflon, stand 310 projecting away from a major surface 312. The stand 310 includes a pair of parallel sidewalls 314 extending substantially perpendicular to the major surface 312 so as to be substantially vertical. A top surface 316 extends substantially perpendicular to the sidewalls 314. The transitions between the top surface 316 and the sidewalls 314 are chamfered to yield angled contact surfaces 318. The width of the stand 310 is carefully controlled relative to the finished surfaces implant 500 so that the implant 500 is only supported by the contact surfaces 318 at pre-selected locations. These locations are selected to avoid pre-finished surfaces and are designated to be finished in later processing steps.

A bracket 320 is fixed to the turnaround support 308 at a first end and supports a proximity switch 322 at a second end. The proximity switch 322 senses whether or not an implant 500 is located on the turnaround support 308.

Figure 14:
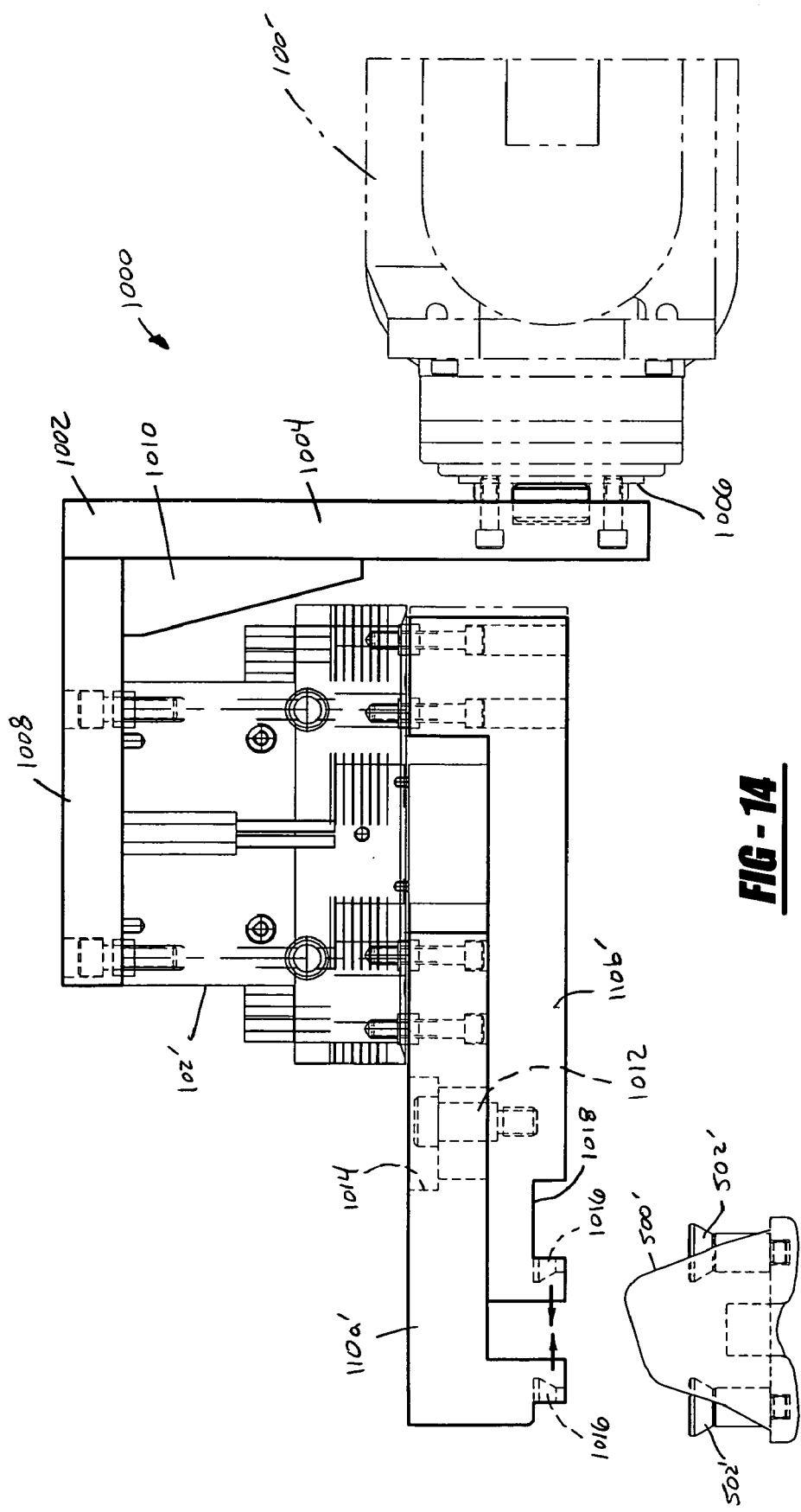
FIG. 14 is a side view of a gripper and finger assembly according to a second embodiment of the present invention.

Referring now to FIG. 14, an alternate embodiment gripper assembly 1000 is shown. The gripper assembly 1000 includes a 90 degree angle bracket 1002 fixed to an end of a robot 100', a gripper 102' fixed to the bracket 1002, and fingers 110' fixed to the gripper 102'. The bracket 1002 includes a first bar 1004 extending perpendicular to an end face 1006 of the robot 100'. A second bar 1008 extends perpendicular to the first bar 1004 and is coupled thereto. A corner flange 1010 is provided at the interface of the first and second bars 1004 and 1008 to increase the strength of the connection therebetween.

The gripper 102' is preferably identical to the gripper 102 of the first embodiment and therefore its description will not be repeated here. The fingers 110' include first and second fingers 110a' and 110b'. The fingers 110' slide open and closed under the operation of the gripper 102'. Inasmuch as the fingers 110' extend perpendicular to the gripper 102', it is preferably that the first finger 110a' is mounted flush to the gripper 102' while the second finger 110b' is offset from the gripper 102' by at least the width of the first finger 110a'.

A guide pin 1012 is fixed to the second finger 110b' and is accommodated by a slot 1014 formed in the first finger 110a'. The guide pin 1012 prevents the first and second fingers 110' from becoming offset relative to one another. In other words, the guide pin 1012 keeps the fingers 110' in a preselected orientation relative to one another.

The first and second fingers 110' include reliefs 1016 which are shaped to complement the clampable surfaces 502' of the knee implant 500'. In the illustrated embodiment the knee implant 500' includes pins that are screwed into the implant 500'. As such, the reliefs 1016 mirror the shape of the screw heads and shafts. A notch 1018 is provided in the second finger 110b' to allow the second finger 110b' to fit over the clampable surface 502' of the implant 500'. Thereafter, the fingers 110' slide outboard to abutingly grip the implant 500' by nesting the clampable pins 502' in the reliefs 1016.

From the foregoing description it can be appreciated that tooling for a direct clamp robotic system is provided. The tooling centers around the provision of fingers for a gripping robot that eliminate the need for an implant support bar to be mounted to each implant. By eliminating the bar, more sophisticated trays and implant reorientation stations can also be employed. This provides an important cost savings measure for implant manufacturers.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A direct clamp tooling set for finishing a part with a robotic finishing system employing a robot having jaws, the tooling set comprising:
   - a pair of opposed L-shaped fingers coupled to the jaw and having clam-shell shaped gripping surfaces adapted to grip at least one vertical projection of the part;
   - a supply stand including chamfered support surfaces supporting the part at first preselected locations; and
   - an implant reorientation station including chamfered support surfaces supporting the part at second preselected locations.

* * * * *